United States Patent [19]

Devon

[11] Patent Number: 5,354,894

[45] Date of Patent: Oct. 11, 1994

[54] PROCESS FOR THE PREPARATION OF LITHIUM DIARYLPHOSPHIDES AND ALKYLATED DERIVATIVES THEREOF

[75] Inventor: Thomas J. Devon, Longview, Tex.

[73] Assignee: Eastman Chemical Company, Kingsport, Tenn.

[21] Appl. No.: 136,051

[22] Filed: Oct. 14, 1993

Related U.S. Application Data

[62] Division of Ser. No. 17,662, Feb. 12, 1993, Pat. No. 5,288,912.

[51] Int. Cl.$^5$ .............................................. C07F 9/50
[52] U.S. Cl. .................................... 568/17; 568/8
[58] Field of Search ......................... 568/9, 17, 8

[56] References Cited

U.S. PATENT DOCUMENTS 3,414,624 12/1968 Peterson et al. ..................... 568/9
3,423,468 1/1969 Zorn et al. ........................... 568/17

OTHER PUBLICATIONS

Chatt et al, Journal of the Chemical Society, (1960), 1378–1389.

*Primary Examiner*—Johann Richter
*Assistant Examiner*—Margaret J. Page
*Attorney, Agent, or Firm*—J. Frederick Thomsen; Harry J. Gwinnell

[57] ABSTRACT

Disclosed is a process for the preparation of alkali metal diarylphosphide compounds wherein at least one of the aryl radicals is substituted with an alkyl group. Also disclosed is the preparation of alkyl(diaryl)phosphine compounds which are obtained by the reaction of the alkali metal diarylphosphide compounds with alkyl halide alkylating agents.

5 Claims, No Drawings

PROCESS FOR THE PREPARATION OF LITHIUM DIARYLPHOSPHIDES AND ALKYLATED DERIVATIVES THEREOF

This is a divisional application of copending application Ser. No. 08/017,662 filed Feb. 12, 1993, now U.S. Pat. No. 5,288,912.

This invention pertains to a novel process for the preparation of alkali metal diarylphosphide compounds wherein at least one of the aryl radicals is substituted with an alkyl group. This invention also pertains to the preparation of alkyl(diaryl)phosphine compounds which are obtained by the reaction of the alkali metal diarylphosphide compounds with alkyl halide alkylating agents.

Trisubstituted phosphine compounds are widely used as ligands in catalyst systems which include one or more Group VIII metals, e.g. palladium and rhodium. Such phosphine compounds in which one or two of the substituents is an alkyl-substituted aryl radical can be utilized in catalyst systems having unique properties. Such catalyst systems may be made particularly useful by controlling the amount of steric crowding around the phosphorus atom, or by having certain electronic donation properties imparted on the phosphorus atom by controlling the position of the alkyl group on the aryl group attached to the phosphorus atom. Such control can modify catalyst performance in the low-pressure, rhodium-catalyzed hydroformylation of olefins. Examples of other catalyst systems where such control can be useful include rhodium-catalyzed hydrogenation of olefins and nickel-catalyzed oligiomerization of olefins.

Various symmetrical triorganophosphine compounds, i.e., trisubstituted phosphines, may be synthesized according to known procedures. One procedure involves the reaction of either Grignard reagents or organolithium reagents with phosphorus trichloride. Such procedures are described in U.S. Pat. Nos. 3,036,132, 3,099,691, 3,949,000 and 4,045,494. Another method that is suitable only for the preparation of trialkyl organophosphines relies on the reaction of phosphine ($PH_3$) with olefins. The rational preparation of tri-organophosphines having two or three different groups attached to the phosphorus atom is more difficult.

Di-o-tolyl(phenyl)phosphine may be prepared by the reaction of 1 mole of dichloro(phenyl)phosphine with 2 moles of the Grignard reagent 2-chloromagnesiumtoluene. Di-p-tolyl(n-propyl)phosphine similarly may be made by the reaction of 2 moles of 4-chloromagnesiumtoluene with dichloro(n-propyl)phosphine. This technique is limited by the availability of organophosphorus precursors having two halogen atoms attached to the phosphorus atom. Another means for preparing di-tolyl-substituted, tertiary organophosphines consists of the reaction of 1 mole of Grignard, or other organometallic, reagent with 1 mole of chloro(di-tolyl)phosphine. For example, a dilithium reagent, e.g., 1,1'-di-lithioferrocene, may be reacted with chloro(diaryl)phosphine reagents such as chloro(di-4-chlorophenyl)phosphine to prepare di-organophosphines such as 1,1'-bis-[di(4-chlorophenyl)phosphino]ferrocene. This procedure and the synthesis of the organophosphorus precursor are disclosed in U.S. Pat. No. 4,152,344. The preparation of chloro(diaryl)phosphine compounds is a difficult procedure requiring multiple steps, as disclosed by J. J. Bishop et al. in J. Organomet. Chem., 27, 241 (1971). Also, this method may be used to prepare only chloro(diaryl)phosphine compounds that have equivalent aryl groups.

A method that is particularly useful in the preparation of triorganophosphine compounds having two phenyl groups attached to the phosphorus atom uses the reaction of lithium metal with triphenylphosphine to prepare lithium diphenylphosphide [J. Chatt et al., J. Chem. Soc. (1960) 1385]. The lithium diphenylphosphide may be reacted with various alkyl halide alkylating agents such as benzyl chloride or n-butyl bromide to produce a tertiary organophosphine having two phenyl groups attached to the phosphorus atom. The initial lithium cleavage reaction co-produces phenyllithium which must be destroyed selectively before the reaction with the alkylating agent can take place. In practice, the final cleavage product mixture of phenyllithium and lithium diphenylphosphide is treated with a masked hydrohalogenation reagent such as tertiary butyl chloride. This reagent reacts selectively with the phenyllithium to produce benzene, lithium chloride and 2-methylpropylene.

As stated above, the phenyllithium must be removed prior to the reaction of the lithium diphenylphosphide with an alkylating reagent to prevent undesirable side reactions from taking place that greatly lower the yield of the desired triorganophosphine compound. The tertiary butyl chloride cannot be present during the reaction of lithium metal with triphenylphosphine because it reacts directly with lithium metal and does not permit the cleavage reaction to take place.

I have found that the application of this lithium cleavage procedure to methyl-substituted triarylphosphines, e.g., tri-p-tolylphosphine, produces results significantly inferior to those obtained when triphenylphosphine is used in the procedure. For example, the yields of the ultimate triorganophosphine product are lower and the lithium does not completely dissolve, even when the cleavage reaction is carried out at temperatures above the ambient temperatures that are normally used. The color of the resulting cleavage mixture is brown, a color that remains even after the subsequent reaction with tertiary butyl chloride. The color of the triphenylphosphine cleavage mixture is usually red-orange in color. The dark color of the cleavage mixture of the tri-p-tolylphosphine cleavage mixture indicates a number of unwanted side reactions take place that are reflected in the low yield and lower purity of the final triorganophosphine following reaction with the alkylating reagent.

I have discovered that lithium diarylphosphide compounds having the structure

(I)

may be obtained in improved yield and/or purity by contacting a triarylphosphine having the formula

(II)

with lithium and a primary or secondary amine in the presence of an inert, organic solvent, wherein $R^1$ is alkyl-substituted aryl and $R^2$ and $R^3$ independently are selected from phenyl and alkyl-substituted aryl. The improvements provided by the present invention are believed to be due to the suppression of certain unknown side reactions caused by the accumulation of the aryllithium cleavage co-product in the crude cleavage mixture. For example, these aryllithium compounds may possibly react with unreacted tri-tolylphosphine by the abstraction of one of the benzylic protons of the methyl groups on the phosphorus compound forming an undesired anionic species that yields undesirable side products. The primary or secondary amine which is present in the process of the invention probably reacts specifically with the aryllithium compounds to form lithium amide compounds and the aromatic hydrocarbon derivative of the aryllithium compound. The lithium amide compound apparently is not as strong a base as the aryllithium compound and thus does not abstract benzylic protons of the methyl groups of the unreacted tri-tolylphosphine and thereby eliminates that unwanted side reaction.

In the first embodiment of the present invention wherein a triarylphosphine of formula (II) is contacted with lithium and an amine, the amount of lithium metal employed may range from about 10 to 1 moles lithium per mole of the triarylphosphine, preferably about 2.2 to 1.8 moles lithium per mole of the triarylphosphine. The particular primary or secondary amine employed in the process is not critical but preferably exhibits good solubility in the solvent used and contains no substituents which are reactive with lithium. Thus, the preferred amines only contain alkyl, cycloalkyl and/or aryl groups attached to the nitrogen atom that have no heteroatom substitution or acidic groups that would react with the lithium. Also, the amine used should form a lithium amide salt that is soluble in the solvent so as not to coat the surface of the metal and stop further dissolution of the lithium.

The alkyl group or groups of the alkyl-substituted aryl groups represented by $R^1$, $R^2$ and $R^3$ contains a benzylic hydrogen atom and up to about 10 carbon atoms. The aryl moiety of such alkyl-substituted aryl radicals may contain from about 6 to 12 carbon atoms, e.g., phenyl, naphthyl, biphenylyl and the like. The aryl moiety preferably is phenyl and tolyl constitutes the alkyl-substituted aryl group which is particularly preferred.

The primary and secondary amines employed in the present invention preferably have a molecular weight in the range of about 31 to 1000 and conform to the general formula

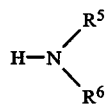
(V)

wherein $R^5$ is hydrogen or an alkyl, cycloalkyl or aryl radical and $R^6$ is an alkyl, cycloalkyl or aryl radical. Primary and secondary amines containing up to about 12 carbon atoms are especially preferred. The amount of the amine employed normally is at least 0.5 mole per mole of triarylphosphine present with amine:triarylphosphine mole ratios of 1:1 to 1.1:1 being preferred.

The inert, organic solvent may be selected from various materials such as aliphatic and cyclic ethers containing up to about 10 carbon atoms. Examples of such solvents include dimethyl ether, diethyl ether, di-isopropyl ether, di-n-butyl ether, 1,4-dioxane and, especially, tetrahydrofuran. The amount of solvent used can be varied substantially but typically the weight ratio of triarylphosphine:solvent is in the range of about 1:3 to 1:1000. The cleavage reaction may be carried out at a temperature of about $-50°$ to $80°$ C. with the range of $0°$ to $30°$ C. being preferred. Pressure normally is not an important factor in the operation of the cleavage process and thus pressures moderately above or below ambient pressure may be used.

A second embodiment of the invention provides a three-step process, including the preparation of a lithium diarylphosphide compound as described hereinabove, for the synthesis of triorganophosphine compounds. The second embodiment thus pertains to a process for the preparation of a triorganophosphine having the formula

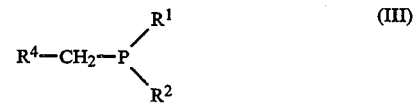
(III)

which comprises the steps of:
(1) contacting a triarylphosphine having the formula

(II)

with lithium and a primary or secondary amine in the presence of an inert solvent to obtain an intermediate product solution of a lithium diarylphosphide compound having the structure

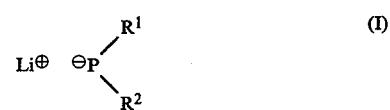
(I)

(2) contacting the intermediate product solution of step (1) with a masked hydrohalogenation agent; and
(3) contacting the product solution of step (2) with an alkylating agent having the formula

(IV)

wherein $R^1$ is alkyl-substituted aryl and $R^2$ and $R^3$ independently are selected from phenyl and alkyl-substituted aryl, $R^4$ is an organic radical or Z, i.e., $R^4-CH_2-$ is the residue of an organic alkylating agent, and Z is a nucleophilic leaving group. Formula (III) encompasses a substantial number of known phosphine compounds which have been employed in various catalyst systems.

The operation of the first step of the process has been described in detail hereinabove. In the second step of the process the intermediate product solution produced in the first step is contacted with a masked hydrohalogenation agent to convert any lithium aryl and/or lithium amide compounds present to non-reactive lithium halides. The omission of step (2) would result in the undesired reaction of the alkylating agent of formula (IV) with lithium aryl and/or lithium amide compounds present in competition with the desired lithium diarylphosphide compound. Such undesired reactions cause purification problems and the inefficient utilization of the alkylating agent.

The masked hydrohalogenation compounds which may be employed are secondary and tertiary alkyl halides which readily form an olefin and a halide salt by the base elimination of hydrogen halide from the compound. These masked hydrohalogention compounds are illustrated by compounds conforming to general formula (VI):

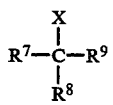
(VI)

wherein $R^7$ is alkyl, cycloalkyl or aryl, $R^8$ is alkyl, $R^9$ is hydrogen or alkyl, and X is a halogen atom, e.g., chloro, bromo or iodo. The alkyl groups which $R^7$, $R^8$ and $R^9$ can represent may contain up to about 8 carbon atoms and include phenyl-substituted alkyl such as benzyl. Cyclohexyl, alkyl-substituted cyclohexyl, phenyl and phenyl substituted with alkyl, alkoxy or halogen are examples of the cycloalkyl and aryl groups which $R^7$ may represent. The preferred masked hydrohalogention compounds are the compounds of formula (VI) having a total of about 3 to 8 carbon atoms and wherein $R^7$ and $R^8$ are independently selected from alkyl groups containing up to about 4 carbon atoms; $R^9$ is hydrogen or an alkyl group containing up to about 4 carbon atoms; and X is chloro or bromo. Tertiary butyl chloride, isopropyl bromide and α-chloroethylbenzene are examples of specific masked hydrohalogention compounds which may be utilized in the process. The amount of masked hydrohalogenation compound used typically is in the range of 0.9 to 1.1 moles per mole of triarylphosphine (II) employed in the first step.

The temperatures at which the second step is carried out typically are in the range of about −50° to 80° C. with the preferred range being about 20° to 40° C. As in the case of the step (1) procedure, pressure normally is not an important factor in the second step and thus pressures moderately above or below ambient pressure may be used. The step (2) procedure conveniently is performed in the presence of the solvent which is used in the first step. However, a different or additional solvent may be used if desired.

The second step of the process wherein the lithium aryl and/or lithium amide compounds are converted to other materials may range from 1 minute to 24 hours after the addition of the masked hydrohalogention compound has been completed, although periods of about 30 to 120 minutes normally are adequate. The completion of the Step (2) reaction(s) may be determined by various means, e.g., by the termination of heat of reaction or by the cessation of the evolution of olefin gas when the masked hydrohalogention compound employed generates a volatile olefin upon reaction with the lithium compound.

In the third step of the process lithium diarylphosphide (I) is reacted with alkylating agent (IV) to produce triorganophosphine (III). The alkylating agents having formula:

$$R^4—CH_2—Z \qquad (IV)$$

are known compounds and/or can be prepared according to conventional procedures. Thus, $R^4$ may represent hydrogen or a wide variety of alkyl, cycloalkyl and aryl radicals which may be unsubstituted or substituted with one or more groups which are not reactive with the lithium diarylphosphide reactant and Z is a nucleophilic leaving group such as a halogen atom, e.g. chloro, bromo or iodo, or a sulfonate ester group such as trifluoromethanesulfonate, toluenesulfonate and bromobenzenesulfonate. Examples of inert functional groups which may be included in organic radical $R^4$ are ether, e.g., alkoxy, cycloalkoxy and aryloxy groups; ester, e.g., alkanoyloxy, cycloalkanoyloxy, aroyloxy, alkoxycarbonyl and cycloalkoxycarbonyl groups; sulfide, e.g., alkylthio, cycloalkylthio and arylthio groups; cyano; keto, e.g., alkanoyl and aroyl groups; and the like. In addition to such inert functional groups, radical $R^4$ may contain one or more —$CH_2$—Z groups which result in the formation of triorganophosphine compounds containing a plurality of diarylphosphino groups. $R^4$ also may represent one of the nucleophilic leaving groups which Z may represent which permits the formation of bis(diarylphosphino)methane compounds. Examples of alkylating agents which may be used in the process may be found in U.S. Pat. No. 4,755,624, 4,760,194, 4,824,977 4,879,416, and 4,904,808.

Preferred alkylating agents have the general formulas:

$$R^{10}—CH_2—Z \qquad (VII)$$

and $$Z—CH_2—R^{11}—CH_2—Z \qquad (VIII)$$

wherein $R^{10}$ is straight- or branched-chain alkyl of up to 6 carbon atoms which may be substituted, for example, with phenyl, or $R^{10}$ may be cycloalkyl such as cyclohexyl; $R^{11}$ is a chemical bond or an organic divalent linking group such as straight- or branched-chain alkylene of up to about 20 carbon atoms or a biarylene radical having the formula —Ar—Ar— wherein each Ar is independently selected from phenylene and naphthylene, preferably ortho-phenylene and ortho-napthylene; and each Z is a halogen atom such as chloro or bromo. The triorganophosphines obtained from alkylating agents (VII) and (VIII) in accordance with my invention have the formulas:

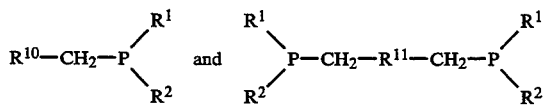

wherein $R^1$, $R^2$, $R^{10}$ and $R^{11}$ are defined above. The alkylation reaction of step (3) may be carried out at temperatures in the range of −100° to 100° C. with the range of about −20° to 25° C. being preferred. The pressures and solvents which may be employed are the same as those of the second step of the process.

The process of the invention is further illustrated by the following examples. The apparatus used in Examples 1-17 and in Comparative Example 1 consisted of a dry 500-milliliter (mL) round bottom, three-necked flask that was equipped with a bare steel magnetic stirring bar, argon atmosphere and a pressure equalizing 50 mL addition funnel. The lithium used was in the form of wire freshly cut into small pieces weighing approximately 0.03 grams each. The abbreviations have the following meanings: g=grams, mL=milliliter, mmol=millimole, and THF=tetrahydrofuran. The THF used was distilled from a THF/potassium/diphenyl ketone mixture. Melting points were determined using sealed glass capillary tubes under nitrogen. Phosphorus 31 nuclear magnetic resonance spectra were obtained using standard equipment known to those skilled in the art.

EXAMPLE 1

The flask was charged with tri-orthotolylphosphine (6.09 g, 20 mmole), lithium (0.28 g, 40 mmol) and THF (50 mL). Dry diisopropylamine (2.02 g, 20 mmol) was syringed into the flask and the mixture was stirred at room temperature for 18 hours. About 98 percent of the lithium had dissolved leaving a bright red-orange solution of the lithium diarylphosphide and the lithium organoamide. The lithium diarylphosphide product has the structure:

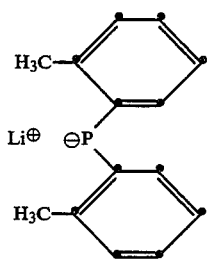

A mixture of THF (10 mL) and tertiary butyl chloride (1.85 g, 20 mmole) was added dropwise to the stirred lithium diarylphosphide mixture at room temperature over a 30 minute period, then was warmed to 40° C. for 30 minutes and then cooled to room temperature. The color of the solution remained bright red-orange.

Thirty-five mL of a solution of 2,2'-bis(bromomethyl)-1,1'-biphenyl (3.40 g, 10 mmol) in THF was prepared and added dropwise to the stirred solution of the lithium diarylphosphide cooled externally in a water-ice bath until the orange color just disappeared. A total of 29.5 mL of the alkylating agent solution (84% of total) was added. The mixture was quenched with 2 mL of methanol. The solvent was removed by sweeping the warmed flask with nitrogen, leaving a crystalline residue. Methanol (50 mL) was added to the flask and the solid was heated to reflux and the slurry then was cooled with stirring. The solid product was filtered under a nitrogen atmosphere, washed with 25 mL of methanol and dried under nitrogen. The net weight of white crystalline triorganophosphine product was 4.80 g (79.2 percent of theoretical yield). The product, 2,2'-bis[(di-orthotolyl)phosphinomethyl]-1,1'-biphenyl, has the structure:

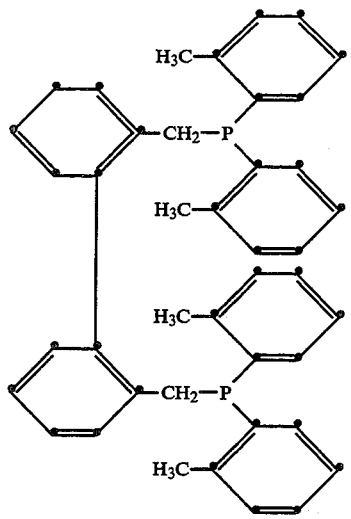

EXAMPLE 2

The flask was charged with tri-orthotolylphosphine (6.09 g, 20 mmol), lithium (0.28 g, 40 mmole) and THF (50 mL). Dry cyclohexylamine (1.98 g, 20 mmole) was syringed into the flask and the mixture was stirred for 18 hours at room temperature. All the lithium metal had dissolved leaving an orange solution with a small amount of yellow solids. A solution of THF (10 mL) and tertiary butylchloride (1.85 g, 20 mmol) was added to the stirred anion mixture over 30 minutes at room temperature. The yellow solid disappeared leaving a clear orange solution of the lithium diarylphosphide compound. The mixture was chilled using a water-ice bath for the next step.

A solution of 2,2'-bis(bromomethyl)-1,1'-biphenyl (3.40 g, 20 mmol) in THF having a total volume of 35 mL was added dropwise to the stirred solution of the lithium diarylphosphide compound at 0° C. over 65 minutes until the orange color just disappeared. The amount of alkylating agent solution added was 85% of the total solution. The crude product mixture was warmed to room temperature and then warmed and swept with nitrogen to obtain an oily residue. Methanol (50 mL) was added to the flask and the contents were heated to gentle reflux with stirring. The product began to crystallize when the methanol contacted the residue. The crystalline slurry was cooled with stirring to room temperature, filtered under a nitrogen atmosphere, washed with 25 mL of methanol and dried under nitrogen. The net weight of the crystalline triorganophosphine product, 2,2'-bis-[(di-orthotolyl)phosphinomethyl]-1,1'-biphenyl, was 4.80 g or a yield 79.2 percent of theoretical.

EXAMPLES 3-6

The procedure of Examples 1 and 2 was repeated using 20 mmol of each of diethylamine (Example 3), pyrollidine (Example 4), n-butylamine (Example 5), and N-ethyl-m-toluidine (Example 6) to prepare lithium di-orthotolylphosphide and convert the phosphide to the triorganophosphine 2,2'-bis[(di-orthotolyl)phosphinomethyl]-1,1'-biphenyl. The yields of triorganophosphine product as a percent of theory obtained were:

| | |
|---|---|
| Example 3 | 64.5 |
| Example 4 | 58.4 |
| Example 5 | 73.4 |
| Example 6 | 64.5 |

Comparative Example 1

This example illustrates the inferior results obtained when the lithium cleavage process is carried out in the absence of a primary or secondary amine.

The flask was charged with tri-orthotolylphosphine (6.09 g, 20 mmol), lithium (0.28 g, 40 mmole) and THF (50 mL) and the mixture was stirred at room temperature for 18 hours. Approximately 60-70 percent of the lithium metal had dissolved forming a dark red-brown solution. A solution of tertiary butyl chloride (1.85 g, 20 mmole) and THF (10 mL) was added dropwise to the lithium/phosphine solution over 30 minutes at room temperature and then the resulting mixture was warmed to 40° C. for an additional 30 minutes and then cooled to room temperature. The mixture had lightened slightly to a deep red-orange color and all the lithium had dissolved.

The anion solution prepared as described in the preceding paragraph was cooled externally with a water-ice bath. A solution of 2,2'-bis(bromomethyl)-1,1'-biphenyl (3.40 g, 10 mmol) in THF having a total volume of 35 mL was prepared and added dropwise to the stirred anion solution over about 20 minutes until the orange color of the anion solution just disappeared. The amount of the alkylating agent solution added was 22.5 mL or 64 percent of the total 35 mL. The mixture was warmed to room temperature and 3 mL of nitrogen purged methanol was added to quench any remaining lithium anion that may be present. The solvent in the flask was removed by warming the flask and sweeping with nitrogen to obtain a colorless oily residue. Methanol (50 mL) was added to the residue to dissolve the lithium chloride salts and to induce crystallization of the desired triorganophosphine product. The oil could only be made to crystallize following heating to reflux and seeding with some crystals of the desired product, an indication of a high concentration of organic impurities present in the crude material. The crystals were isolated after cooling the stirred mixture to room temperature and filtering under inert conditions. The crystals were washed with an additional 25 mL of methanol and then dried under nitrogen. The net weight of 2,2'-bis[(di-orthotolyl)phosphinomethyl]-1,1'-biphenyl was 3.02 g (49.8 percent of theoretical yield) as a white crystalline product with a melting point range of 154°-157° C. The phosphorus 31 (31P) absorption of the two equivalent phosphorus atoms was −34.0 parts per million (ppm) relative to aqueous 85 percent phosphoric acid internal standard.

EXAMPLE 7

The flask was charged with tri-paratolylphosphine (12.18 g, 40 mmol), lithium (0.56 g, 80 mmole) and 100 mL of dry distilled THF. Cyclohexylamine (3.97 g, 40 mmol) was syringed into the flask and the mixture was stirred at room temperature for 18 hours At the end of this period all the lithium had dissolved leaving a red-brown solution of the anion mixture including the lithium phosphide having the structure:

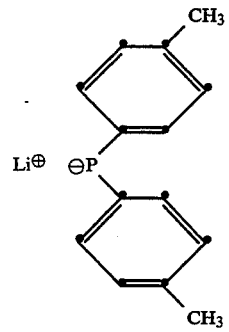

A mixture of tertiary butylchloride (3.70 g, 40 mmol) and tetrahydrofuran (10 mL) was added dropwise to the stirred solution over 30 minutes at room temperature. The mixture obtained was warmed to 40° C. and kept at that temperature for 30 minutes and then cooled to room temperature. The resulting mixture was a bright red-orange color.

A solution of 2,2'-bis(bromomethyl)-1,1'-biphenyl (6.80 g, 20 mmole) in THF having a total volume of 49 mL was prepared and added, with stirring, over a 90 minute period to the solution of the lithium diarylphosphide compound which was chilled externally with a water-ice bath. The solution of the dibromo alkylating agent was added dropwise until the orange color of the anion just disappeared. A total of 41 mL of the solution, or 84 percent of the alkylating agent, was added. The resulting mixture was warmed to room temperature and then quenched with 1 mL of methanol. The flask then was warmed up and swept with nitrogen to remove the solvent, leaving a crystalline solid residue. The residue was recrystallized with 100 mL of nitrogen-purged isopropanol by heating to reflux and then cooling to room temperature with stirring. The recrystallized triorganophosphine was collected by filtration under nitrogen, washed with 50 mL each of isopropanol and methanol and then dried under nitrogen. The net weight of white crystalline product, 2,2'-bis[(di-paratolyl)phosphinomethyl]-1,1'-biphenyl, was 7.75 g or 63.9 percent of theoretical yield. The melting point range was 134°-138° C. The 31P NMR absorption of the two equivalent phosphorus atoms was −12.9 ppm chemical shift relative to an 85 percent aqueous phosphoric acid internal standard.

EXAMPLE 8

The flask was charged with tri-metatolylphosphine (6.09 g, 20 mmole), lithium wire (0.28 g, 40 mmole) and dry distilled THF solvent (50 mL). Diethylamine (1.46 g, 20 mmole) was syringed into the flask and the mixture was allowed to stir at room temperature for 6 hours, dissolving about 90 percent of the lithium. A mixture of THF (10 mL) and tertiary butyl chloride (1.85 g, 20 mmole) was added dropwise to the stirred red-brown solution of the lithium diarylphosphide solution at room temperature over 30 minutes and the resulting solution was stirred at room temperature for an additional 18 hours.

A solution (total volume=21 mL) of 2,2'-bis(bromomethyl)-1,1'-biphenyl (3.40 g, 10 mmole) was added dropwise to the stirred solution of the lithium diarylphosphide compound, chilled in a water-ice bath, over 90 minutes until the red-brown color just disappeared. The amount of alkylating agent solution added was approximately 95% of the total solution. The mixture thus produced was treated with 5 mL of methanol and was stripped of the solvent by purging the flask with nitrogen. The residue was dissolved partially in 100 mL of toluene. This was filtered under nitrogen through a Teflon fiber filter. The filtrate was treated with 100 mL of water in a separatory funnel and the resulting emulsion was filtered by suction through a Celite filter under nitrogen leaving two clear layers. The yellow-green organic layer was separated from the aqueous layer in a separatory funnel. The organic layer was then placed in a round-bottomed flask and stripped of toluene with nitrogen leaving 6.05 g of oily residue. The residue was subjected to a vacuum of 0.15 millimeter mercury pressure and heated to 210° C. in a Kugelrohr apparatus to remove high-boiling but relatively volatile organophosphorus impurities. The flask was cooled under vacuum and yielded the product, 2,2'-bis[(di-metatolyl)phosphinemethyl]-1,1'-biphenyl, as an orange glass net weight 3.92 g or 65 percent of theory.

EXAMPLE 9

In this example, diisopropylamine is used during the lithium cleavage of tri-orthotolylphosphine for the synthesis of 1,2-bis[(di-orthotolyl)phosphino]ethane, a bidentate ligand of high steric crowding.

The flask was charged with tri-orthotolylphosphine (6.09 g, 20 mmole), lithium wire (0.28 g, 40 mmole) and 50 mL of dry distilled THF solvent. Diisopropylamine (2.02 g, 20 mole) was added to the flask by syringe and the mixture was stirred at room temperature for 18 hours. Approximately 95 percent of the lithium had dissolved leaving a dark red-orange solution of the mixed anions. A mixture of tetrahydrofuran (10 mL) and tertiary butyl chloride (1.85 g, 20 mmole) was added to the stirred anion mixture over 30 minutes at room temperature, warmed to 40° C. for an additional 30 minutes and then cooled back to room temperature. The final color of the solution was a red-orange.

The flask containing the diarylphosphide anion was chilled externally with a water-ice bath and a solution of 1,2-dichloroethane (0.99 g, 10 mmole) and 10 mL of THF was added dropwise to the stirred anion solution over 45 minutes until the orange color just disappeared. The amount of alkylating agent solution added was about 95% of the total solution. The reaction mixture then was warmed to room temperature and the solvent was removed by a nitrogen stream sweeping the flask, leaving a white solid residue. Nitrogen-purged methanol (50 mL) was added to the flask and the mixture was warmed to a gentle reflux to dissolve the lithium chloride salts and to "age" the organophosphine product crystals. After cooling with stirring to room temperature, the mixture was filtered under nitrogen and washed with 25 mL of methanol and dried under nitrogen. The product was a white crystalline powder, net weight 3.54 g or 78 percent of theoretical yield, having a melting point range of 153°-154° C. The phosphorus 31 NMR absorption was −34.3 ppm relative to 85 percent aqueous phosphoric acid standard. The triorganophosphine product has the structure:

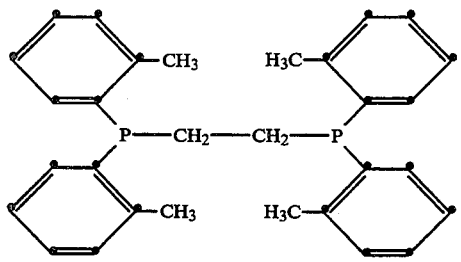

EXAMPLE 10

The flask was charged with tri-orthotolylphosphine (6.09 g, 20 mmole), clean cut lithium wire (0.28 g, 40 mmole) and 50 mL of dry distilled THF solvent. Dry diisopropylamine (2.02 g, 20 mmole) was syringed into the flask and the mixture was stirred at room temperature for 18 hours to give a bright red-orange mixture with approximately 95 percent of the lithium being dissolved. A mixture of tertiary butyl chloride (1.85 g, 20 mmole) and 10 mL of THF was added to the stirred anion mixture at room temperature over 30 minutes. The mixture was warmed to and held at 40° C. for 30 minutes and cooled to room temperature leaving a bright red-orange solution of the diarylphosphide anion.

The flask containing the diarylphosphide anion was chilled externally with a water-ice bath and a solution of 1,3-dibromopropane (2.02 g, 10 mmole) and 9 mL of THF solvent was added dropwise to the stirred anion solution over 30 minutes until the orange color just disappeared. The amount of alkylating agent solution added was about 89% of the total solution. The reaction mixture then was warmed to room temperature and stripped of the solvent using a nitrogen purge. The crude product crystallized as a white solid. Methanol (50 mL) was added to the flask and the mixture was heated with stirring to gentle reflux and cooled over 1 hour back to room temperature. The slurry was filtered under a nitrogen atmosphere and washed with 25 mL of methanol and dried under nitrogen. The white crystalline product, 1,3-bis[(di-orthotolyl)phosphino]propane, was obtained in a yield of 3.37 g or 72% of theory and had a melting point range of 143°-143.5° C. and a phosphorus 31 NMR chemical shift of −39.6 ppm relative to 85 percent aqueous phosphoric acid standard.

EXAMPLE 11

The basic procedure of Example 10 was repeated using tri-orthotolylphosphine (6.09 g, 20 mmole), lithium (0.28 g, 40 mmole) and diisopropylamine (2.02 g, 20 mmole) during the cleavage reaction. The anion mixture was reacted with tertiary butyl chloride (1.85 g, 20 mmole) and the diarylphosphide thus produced was reacted with 1,4-dibromobutane (2.16 g, 10 mole) at water-ice temperatures. Approximately 93 percent of the dibromo alkylating agent was required to quench the color of the organophosphide anion. The crude solid was heated with stirring with 50 mL of methanol as described above and cooled and filtered. The crystalline white product, 1,4-bis[(di-orthotolyl)phosphino]butane, was obtained in a yield of 3.69 g or 76 percent of theory and had a melting point range of 201°-202° C. and a phosphorus 31 NMR chemical shift of −38.7 ppm relative to 85 percent aqueous phosphoric acid.

EXAMPLE 12

This example uses diisopropylamine during the lithium cleavage step in the preparation of the sterically-hindered monodentate organophosphine ligand di-orthotolylbenzylphosphine.

The flask was charged with tri-orthotolylphosphine (6.09 g, 20 mmole), clean cut lithium wire (0.28 g, 40 mmole) and 50 mL of dry THF solvent. Dry diisopropylamine (2.02 g, 20 mmole) was syringed into the flask and the mixture was stirred at room temperature for 18 hours. A mixture of tertiary butyl chloride (1.85 g, 20 mmole) and 10 mL of THF was added dropwise to the stirred anion mixture at room temperature over 30 minutes and the resulting mixture was warmed up to 40° C. and held there for an additional 30 minutes and then cooled to room temperature. The resulting bright red-orange solution was then chilled externally with a water-ice bath.

A solution of benzyl chloride (2.53 g, 20 mmole) and 10 mL of THF solvent was added dropwise to the chilled, stirred anion solution over 20 minutes until the orange color just disappeared. The amount of alkylating agent required was about 92% of the total solution. The reaction mixture then was warmed to room temperature and the THF solvent was stripped away using a nitrogen purge, leaving a white solid residue. Methanol (50 mL) was added to the flask and the mixture was heated to gentle reflux with stirring and then cooled with stirring to room temperature. The slurry of the white crystalline product was filtered under nitrogen and the product collected was washed with 25 mL of methanol and dried under nitrogen. The white crystalline product, di-orthotolyl(benzyl)phosphine, was obtained in a yield of 4.79 g, 79 percent of theory and had a melting point range of 128.5°–130° C. The phosphorus 31 NMR chemical shift was −32.2 ppm relative to 85 percent aqueous phosphoric acid standard.

EXAMPLE 13

This example describes the preparation of a triorganophosphine having three different hydrocarbyl moieties, normally a very difficult synthetic procedure, by the high-yield, selective-lithium cleavage of one orthotolyl hydrocarbon group from phenyl-di-orthotolylphosphine to produce the mixed phenyl-orthotolylphosphide anion in high yield.

The flask was charged with phenyl-di-orthotolylphosphine (5.81 g, 20 mmole), clean cut lithium wire (0.28 g, 40 mmole) and 50 mL of dry THF. Dry diisopropylamine (2.02 g, 20 mmole) was added via syringe and the mixture was stirred at room temperature for 18 hours. The resulting mixture was a dark red-brown color with approximately 95 percent of the lithium having dissolved. A mixture of tertiary butyl chloride (1.85 g, 20 mmole) and 10 mL of THF was added to the stirred anion mixture at room temperature over 30 minutes, warmed to 40° C. and held there for 30 minutes and cooled to room temperature. The resulting dark red-orange solution was then chilled externally with a water-ice bath.

A solution of benzyl chloride (2.53 g, 20 mmole) and 10 mL of THF was added dropwise to the cold, stirred solution of the anion over 20 minutes until the orange color of the anion just disappeared. The amount of alkylating agent required was 92% of the total solution. The mixture was warmed to room temperature and 50 mL of nitrogen-purged water was added to the flask containing the crude product solution in THF. The mixture was stirred and the phases were allowed to separate. The THF layer was analyzed using gas/liquid phase chromatography (GLC). The method used a flame ionization detector instrument with a 30-meter DB-1 medium bore capillary column. The machine had an injection port splitter with a 30/1 split ratio. A 1.0 microliter sample was used for the injection. The temperature program conditions used were a 2 minute initial period at 50° C., followed by a program heat up rate of 8° C. per minute up to 250° C. and a final temperature plateau at 250° C. for 4 minutes. The crude product showed the desired product eluting at 4.80 minutes and the side-product di-orthotolylbenzylphosphine eluting at 5.04 minutes. The area ratios of the two peaks were 90/10 in favor of the desired orthotolyl(phenyl)(benzyl)phosphine.

The organic layer was separated from the aqueous layer in a separatory funnel and washed with an additional 50 mL of water. The THF layer was transferred to a 500-mL, three-necked flask and was purged with a stream of nitrogen to remove the THF leaving a white waxy residue. Methanol (50 mL) was added to the flask along with a magnetic stirrer and heated to gentle reflux and then cooled with stirring to form a white crystalline slurry of the product. This was filtered under nitrogen and washed with an additional 25 mL of methanol and dried under nitrogen. The product was obtained in a yield of 3.61 g (62% of theory) and had a melting point range of 76°–78° C. This material had a phosphorus 31 NMR chemical shift of −21.1 ppm relative to 85 percent aqueous phosphoric acid.

EXAMPLE 14

This and the next two examples illustrate the application of the present invention in the preparation of bis(di-organophosphino)-ligands having an intermediate degree of steric hindrance around the phosphorus centers, i.e., each of the two phosphorus atoms of the ligand compound bears a phenyl and an orthotolyl group. This is a very difficult synthesis if carried out using alternative, known synthetic methods.

The flask was charged with di-orthotolyl(phenyl)-phosphine (5.81 g, 20 mmole), clean cut lithium wire (0.28 g, 40 mmole) and 50 mL of dry THF. Dry diisopropylamine (2.02 g, 20 mmole) was added via syringe and the mixture was stirred at room temperature for 18 hours, during which time approximately 98 percent of the lithium had dissolved forming a red-brown solution. A mixture of tertiary butyl chloride (1.85 g, 20 mmole) and 10 mL of THF was added to the phosphide anion mixture at room temperature over 30 minutes and the mixture was warmed and held at 40° C. for 30 minutes and then cooled to room temperature. The resulting red-orange solution was then chilled externally with a water-ice bath.

A solution of 1,2-dichloroethane (0.99 g, 10 mmole) and 10 mL of THF was added dropwise to the chilled, stirred anion solution over 20 minutes until the orange color just disappeared, which required 86 percent of the dichloroethane to accomplish. This mixture was allowed to warm to room temperature and was then quenched with 50 mL of nitrogen-purged water. The mixture was stirred and the two phases were allowed to separate. A gas/liquid phase chromatographic analysis of the THF layer was carried out using the procedure described in Example 13. The desired product eluted from the column at 8.45 minutes followed by a peak that is probably the side product 1-di-(orthotolyl)phosphino-2-[(phenyl)orthotolylphosphino]ethane that eluted at 8.61 minutes. The area percent ratios of these two products were 4.93/1.00, respectively.

The mixture was transferred to a separatory funnel under nitrogen and allowed to separate into two clear colorless phases. The bottom aqueous layer was drained and discarded. The THF layer was then washed with an additional 50 mL of water and separated again. The THF layer then was added to a 500 mL, three-necked flask and the THF was removed using a nitrogen purge leaving behind a heavy, oily paste. Isopropanol (50 mL) was added to the flask and upon heating the mixture to reflux all of the oil dissolved forming a homogeneous solution. The mixture was induced to crystallize after chilling an aliquot to dry-ice temperatures and then using this to seed the mixture. The mixture was warmed to 40° C. and then cooled slowly to room temperature to increase the crystal size. The product was collected by filtration on a fine Teflon filter pad under nitrogen and washed with 25 mL of methanol and dried under nitrogen. The product was obtained as a white powder in a yield of 1.72 g (40 percent of theory) and had a melting point range of 78°-81° C. The powder was analyzed by the above-described GLC procedure which showed the desired product and the coproduct only, with an area ratio of 5.6/1 in favor of the desired product, 1,2-bis[orthotolyl(phenyl)phosphino]ethane. The phosphorus 31 NMR absorption of the phosphorus atoms of the product was −23.6 ppm relative to 85 percent aqueous phosphoric acid.

EXAMPLE 15

The general procedure described in Example 14 was repeated to prepare 1,3-bis[(phenyl)(orthotolyl)phosphino]propane using diisopropylamine in the lithium cleavage step. The flask was charged with 5.81 g (20 mmole) of phenyl-di-orthotolylphosphine, clean cut lithium wire (0.28 g, 40 mmole) and 50 mL of dry distilled THF. Diisopropylamine (2.02 g, 20 mmole) was syringed in and the mixture stirred at room temperature for 18 hours, when all lithium had by then dissolved. The mixture then was treated with tertiary butyl chloride (1.85 g, 20 mmole) in 10 mL of THF.

A solution of 1,3-dibromopropane (2.02 g, 10 mmole) in 10 mL of THF was prepared and added dropwise over 15 minutes to the lithium diarylphosphide solution, chilled in a water-ice bath, until the orange color just disappeared. This required 82 percent of the dibromo alkylating agent to reach the color end-point. After warming to room temperature, water (100 mL) was added to the flask and the mixture stirred and then allowed to separate into two colorless layers. The crude, upper THF layer was analyzed using the GLC analysis procedure described in Example 13. The analysis showed peaks associated with the desired product, 1,3-bis[(phenyl)(orthotolyl)phosphino]propane, at a retention time of 9.03 minutes, the side-product, (1-(di-orthotolylphosphino)-3-(phenyl-orthotolylphosphino)-propane, with a retention time of 9.19 minutes, and the tetra-orthotolyl side product, with a retention time of 9.34 minutes. The area ratios of these materials were 76.2/18.3/1.0, respectively. The THF solution was separated from the aqueous layer using a separatory funnel and then transferred into a 500 mL three-necked flask, where the solvent was removed by sweeping with nitrogen. Isopropanol (50 mL) was added to the solid residue and the mixture was heated to reflux and then cooled slowly to room temperature to crystallize the product. The product was collected by filtration under nitrogen and was washed with 25 mL of methanol and dried under nitrogen. The product was obtained in a yield of 2.18 g (49.5 percent of theory) and had a melting point range of 120°-122° C. GLC analysis showed that the product comprised the desired product and the side product with a peak area ratio of 3.38/1.0. The phosphorus 31 NMR absorption spectrum showed a peak at −28.4 ppm relative to 85 percent aqueous phosphoric acid.

EXAMPLE 16

The general procedure described in Examples 14 and 15 was repeated to prepare a bis(triorganophosphino) ligand compound having mixed phenyl and orthotolyl groups attached to the two phosphorus atoms. The flask was charged with di(orthotolyl)(phenyl)phosphine (5.81 g, 20 mmole), clean cut lithium wire (0.28 g, 40 mmole) and 50 mL of dry THF. Diisopropylamine (2.02 g, 20 mmole) was added and the mixture was stirred at room temperature for 18 hours. The mixture was treated with 1.85 g (20 mmole) of tertiary butyl chloride in 10 mL of THF as described above.

The diarylphosphide anion mixture was cooled in a water-ice bath and a solution of 1,4-dichlorobutane (1.27 g, 10 mmole) in 10 mL of THF was added dropwise until the orange color of the anion just disappeared, which occurred when 91% of the 1,4-dichlorobutane had been added. After warming to room temperature, the mixture was quenched with 1 mL of methanol. This crude mixture was analyzed using the GLC method described above. The desired product, 1,4-bis[(phenyl)(orthotolyl)phosphine]butane, had an elution time of 9.37 minutes, followed by the trimethyl by-product, 1-[di-(orthotolyl)phosphino]-4-[(phenyl)orthotolylphosphino]butane with a retention time of 9.54 minutes and a trace of the tetramethyl by-product (compound of Example 11) at a retention time of 9.72 minutes. The relative area ratios of the three compounds were 76.4/18.2/1.0, respectively. The THF solvent was removed by sweeping with nitrogen leaving a yellow crystalline residue. Methanol (50 mL) was added to the residue and the mixture was heated with stirring to reflux and cooled to room temperature slowly. The product was collected by filtration under nitrogen and washed with 25 mL of methanol and dried under nitrogen. The white crystalline product was obtained in a yield of 2.87 g (63% of theory) and had a melting point range of 133°-136° C. GLC analysis showed the area ratio of the product peak to that of the trimethyl by-product to be 4.15/1.0. The phosphorus 31 NMR absorption for the two phosphorus atoms of the product was −27.4 ppm relative to 85 percent aqueous phosphoric acid.

EXAMPLE 17

The flask was charged with tri-orthotolylphosphine (6.09 g, 20 mmole), clean cut lithium wire (0.28 g, 40 mmole) and 50 mL of dry THF. Diisopropylamine was added and the mixture was stirred at room temperature for 24 hours at which time approximately 95 percent of the lithium had dissolved. The crude anion mixture then was reacted with tertiary butyl chloride (1.85 g, 20 mmole). The solution of the diarylphosphide anion was chilled in a dry-ice isopropanol bath that was kept between −45° C. and −40° C. by the addition of pieces of dry-ice to the bath.

A solution of 2-(bromomethyl)benzoic acid methyl ester (4.58 g, 20 mmole) and sufficient THF solvent to make a total volume of 25 mL was prepared and was added dropwise over 60 minutes to the cold, stirred anion mixture. The color of the mixture lightened to a yellow-orange color that persisted to the end of the addition. The mixture was warmed to room temperature and then quenched with 1 mL of methanol. There was no color change. The solvent was swept away with nitrogen, leaving a sticky, yellow solid. Methanol (50 mL) was added to the residue and the mixture was heated to reflux. A white suspension formed and the mixture was cooled to room temperature with stirring. The solids were filtered under nitrogen and washed with 25 mL of methanol and dried under nitrogen. The product, 2-(methoxycarbonyl)benzyl-di-(orthotolyl)-phosphine, was obtained as a white powder in a yield of 3.63 g (50% of theory) and had a melting point range of 132°–136° C. and a GLC retention time of 6.29 minutes using the chromatographic procedure described in Example 13.

Utility Examples 1–3 show how changing the position of methyl groups on the aryl groups attached to the phosphorus atom of phosphine ligand compounds can change the isomer selectivity of a low pressure rhodium hydroformylation catalyst in the hydroformylation of propylene. The hydroformylation reactor employed consisted of a 4-foot tall by 1-inch inside diameter stainless steel pipe mounted vertically. The reactor has a stainless steel filter element at the bottom welded into the side of the pipe that is connected to a feed line for the propylene, hydrogen, carbon monoxide and nitrogen that is fed to the unit. The bottom of the reactor is connected via ¼-inch Aminco tubing to a piping cross. This cross is connected by valves and tubing to: (1) a pump that is used to feed the process solvent (2,2,4-trimethylpentane-1,3-diol monoisobutyrate) to maintain reactor catalyst volume; (2) a drain valve; and (3) a liquid leg connected to the high pressure side of a differential pressure (D/P) cell for measuring catalyst volume. The top of the reactor pipe has a screwed plug that has a thermowell in it that fits axially with the pipe for measuring catalyst temperature. The plug also is removed for the addition of catalyst to the reactor. The reactor is heated by a circulating oil bath.

The propylene is fed to the unit from a calibrated feed tank via a high pressure rotameter as a liquid. The gaseous feeds are fed by either flow control valves or by a rotameter. All feeds pass through a preheater to vaporize the propylene before entering the reactor through the filter element entry point. The catalyst solution is contained in the bottom of the reactor pipe where the reactants bubble up through the catalyst solution and react to produce butyraldehyde product. The aldehyde product leaves the reactor as a vapor along with the unreacted gaseous feedstock out the top of the reactor through a "T" near the top of the pipe. The gases are cooled in a high pressure heat exchanger and the butyraldehyde product collects as a liquid in a high pressure vapor liquid separator. The uncondensed gases are dropped to atmospheric pressure through a pressure control valve and pass through a series of dry-ice traps to collect more butyraldehyde product.

The butyraldehyde product is collected from the separator and the dry-ice traps hourly during the run in tared bottles. The dissolved propylene is allowed to degas at room temperature for 1 hour. The net weight of crude product is determined by weight difference and is analyzed by standard GLC techniques to determine the purity of the crude product and the ratio of the n-butyraldehyde to isobutyraldehyde isomers in the product (N/Iso ratio).

Utility Example 1

A catalyst solution was prepared from rhodium 2-ethylhexanoate (Rh-2EH) containing 25 milligrams (mg, 0.243 mmol) of rhodium as the metal, 2,2'-bis[di-(paratolyl)phosphino]-1,1'-biphenyl (0.74 g, 1.215 mmole) and 190 mL of 2,2,4-trimethylpentane-1,3-diol monoisobutyrate solvent under nitrogen. All manipulations of the catalyst solution were carried out under either nitrogen or argon blanketing conditions. The catalyst solution was charged to the reactor pipe under argon and the reactor then sealed. The reactor was pressured to 260 pounds per square inch gauge (psig) with hydrogen, carbon monoxide and nitrogen and then heated to 105° C.

Upon reaching the 105 degree reaction temperature, the flows were adjusted to hydrogen=4.31 liters per minute at standard temperature and pressure (L/min STP);
carbon monoxide=1.44 L/min STP;
nitrogen=0.96 L/min STP, and
propylene=2.88 L/min STP.

These flows were maintained at the above pressure and temperature for 5 hours. The butyraldehyde product was collected hourly and analyzed. The average yield of butyraldehyde for the last 3 hours of the run was 68.6 g of butyraldehyde isomers per hour or a catalyst activity of 6.05 pounds of butyraldehyde per gram of rhodium per hour (lb HBu/g Rh-hr). The average N/Iso ratio for this product was 43.1/1.

Utility Example 2

A catalyst solution was prepared from Rh-2EH (containing 25 mg of rhodium, 0.243 mmole), 2,2'-bis[di-(orthotolyl)phosphino]-1,1'-biphenyl (0.74 g, 1.215 mmole) and 190 mL of 2,2,4-trimethylpentane-1,3-diol monoisobutyrate solvent. The catalyst solution was charged to the reactor as described in the preceding example. The reactor was pressured to 260 psig with hydrogen, carbon monoxide and nitrogen and heated to 105° C. Upon reaching 105° C., the flows were adjusted to hydrogen=4.31 L/min STP;
carbon monoxide=1.44 L/min STP;
nitrogen=0.96 L/min STP, and
propylene=2.88 L/min STP.

The run was carried out in the same manner as the preceding example. The average amount of butyraldehyde produced in the last 3 hours of operation was 41.7 g per hour, equivalent to a catalyst activity of 3.68 pounds butyraldehyde per gram rhodium per hour. The average N/Iso ratio was 1.72/1.

Utility Example 3

This example describes the use of a catalyst system comprising 2,2'-bis[di-(paratolyl)phosphino]-1,1'-biphenyl ligand and rhodium in the hydroformylation of octene-1 to produce isomeric nonanal with a high selectivity to the linear product (TX-1903-119). The reactor was a stainless steel tube 3 feet tall by 1 inch inside diameter. The tube had a ¼-inch pipe section welded into the side 6 inches from the bottom that was the liquid overflow outlet for the reactor. The bottom of the reactor was connected to a cross having concentric piping around ¼-inch stainless steel tubing having a sintered stainless steel frit welded on to the end of it and positioned on the bottom of the reactor. This was for the gaseous feeds to the reactor. The annulus space around the ¼-inch tubing was where the liquid feeds to the unit, namely catalyst solution and octene-1 feed entered the reactor.

The cross was connected to the two liquid feed pumps, the liquid leg for the level control D/P cell and a drain valve for the reactor. The level was controlled by a valve on the overflow outlet pipe that drained catalyst from the reactor to hold a constant level in the reactor. The reactor was heated with circulating oil in the jacket welded around the reactor and temperature was recorded via thermocouples placed in a thermowell inside the reactor. The top of the reactor was connected to a condenser to collect any material that was vaporized overhead with the unreacted gaseous feeds. The gases were dropped to atmospheric pressure via a pressure control valve and passed through a series of dry-ice traps. The gaseous hydrogen, carbon monoxide and nitrogen feeds were fed to the unit via Brooks flow controllers. The liquid catalyst and product overflows into a calibrated glass product tank. Any condensable organic compounds that are liquified by the overhead condenser are collected in a high pressure V/L separator and are periodically drained into the tank containing the overflow product.

A catalyst feed solution was prepared from Rh2-EH (containing 100 mg Rh, 0.97 mmole), 2,2'-bis[di-(paratolyl)phosphino]-1,1'-biphenyl (1.47 g, 2.43 mmole) and 500 mL of 2,2,4-trimethylpentane-1,3-diol monoisobutyrate solvent. The reactor was pressured to 200 psig with feed gases set at the following feed rates:
hydrogen=1.50 L/min STP,
carbon monoxide=1.00 L/min STP, and
nitrogen=0.50 L/min STP.

The catalyst solution was added to the catalyst pump feed tank and was pumped into the reactor to a catalyst volume level of 100 mL. The reactor temperature was then brought to 95° C. Upon reaching 95°, the catalyst pump was set at a feed rate of 100 mL per hour and the octene-1 feed pump was also started at a 100 mL (71.5 g) per hour feed rate. These pumping rates were continued for a 2-hour period. The reactor level control valve was set at a 200-mL volume and allowed catalyst and product to overflow into the product tank. The liquid feeds were stopped at 2 hours but the gases were continued to be fed at 95 degrees and 200 psig for an additional 2 hours.

The overflow product was collected in a tared bottle and analyzed by standard GLC techniques. The catalyst/product solution in the reactor was drained separately out the bottom of the reactor and analyzed in a similar manner. A total of 200 mL (143 g, 1,275 moles) of octene-1 was fed to the unit. The yield of nonanal isomer product was 126.8 g with a linear to branched ratio of 50.1/1. The yield of isooctane was 10.8 g and the yield of octane was 2.26 g. The conversion of 1-octene was 77.9 percent of the total fed.

The invention has been described in detail with particular reference to preferred embodiments thereof, but it will be understood that variations and modifications can be effected within the spirit and scope of the invention.

I claim:

1. Process for the preparation of lithium diarylphosphide compounds having the structure

which comprises contacting a triarylphosphine having the formula

with lithium and a primary or secondary amine in the presence of an inert, organic solvent, wherein $R^1$ is alkyl-substituted aryl and $R^2$ and $R^3$ independently are selected from phenyl and alkyl-substituted aryl.

2. Process according to claim 1 wherein the amount of lithium employed is about 10 to 1 moles of lithium per mole of the triarylphosphine, the alkyl groups of the alkyl-substituted aryl groups contain a benzylic hydrogen atom and up to about 10 carbon atoms, and the aryl moiety of the alkyl-substituted aryl groups contain from 6 to 12 carbon atoms.

3. Process according to claim 2 wherein the amine has a molecular weight of 31 to 1000, the inert solvent is an aliphatic or cyclic ether containing up to about 10 carbon atoms and the contacting is performed at about −50° to 80° C.

4. Process for the preparation of lithium diarylphosphide compounds having the structure

which comprises contacting a triarylphosphine having the formula

with lithium and a primary or secondary amine having a molecular weight of 31 to 1000 and the formula

wherein $R^5$ is hydrogen or an alkyl, cycloalkyl or aryl radical and $R^6$ is an alkyl, cycloalkyl or aryl radical at a temperature of about −50° to 80° C. in the presence of an inert, organic solvent, selected from aliphatic and cyclic ethers containing up to about 10 carbon atoms, wherein the amount of lithium employed is about 10 to 1 moles of lithium per mole of the triarylphosphine, $R^1$ is alkyl-substituted aryl and $R^2$ and $R^3$ independently are selected from phenyl and alkyl-substituted aryl in which the alkyl groups of the alkyl-substituted aryl groups contain a benzylic hydrogen atom and up to about 10 carbon atoms, and the aryl moiety of the alkyl-substituted aryl groups contain from 6 to 12 carbon atoms.

5. Process for the preparation of lithium diarylphosphide compounds having the structure

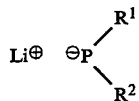 (I)

which comprises contacting a triarylphosphine having the formula

 (II)

with lithium and a primary or secondary amine having the formula

 (V)

wherein $R^5$ is hydrogen or alkyl of up to about 12 carbon atoms and $R^6$ is alkyl of up to about 12 carbon atoms, at a temperature of about 0° to 30° C. in the presence of tetrahydrofuran solvent, wherein the amount of lithium employed is about 2.2 to 1.8 moles of lithium per mole of the triarylphosphine, $R^1$ is tolyl and $R^2$ and $R^3$ independently are selected from phenyl and tolyl.

* * * * *